US007922680B2

(12) United States Patent
Nordt, III et al.

(10) Patent No.: US 7,922,680 B2
(45) Date of Patent: *Apr. 12, 2011

(54) METHOD OF MAKING WRIST SUPPORT FOR JOINT POSITIONING

(75) Inventors: William E. Nordt, III, Charles City, VA (US); Ian D. Kovacevich, Charlotte, NC (US); Kevin J. Dahlquist, Charlotte, NC (US); Tom J. Philpott, Charlotte, NC (US)

(73) Assignee: Nordt Development Company, LLC, Charles City, VA (US)

( * ) Notice: Subject to any disclaimer, the term of this patent is extended or adjusted under 35 U.S.C. 154(b) by 421 days.

This patent is subject to a terminal disclaimer.

(21) Appl. No.: 11/876,578

(22) Filed: Oct. 22, 2007

(65) Prior Publication Data

US 2008/0039767 A1    Feb. 14, 2008

Related U.S. Application Data

(63) Continuation of application No. 11/187,589, filed on Jul. 22, 2005, now Pat. No. 7,704,219, which is a continuation-in-part of application No. 29/209,985, filed on Jul. 22, 2004, now Pat. No. Des. 520,141.

(60) Provisional application No. 60/590,941, filed on Jul. 22, 2004.

(51) Int. Cl.
*A61F 5/00* (2006.01)
*A61F 13/00* (2006.01)

(52) U.S. Cl. ........... 602/21; 602/5; 602/20; 602/64

(58) Field of Classification Search .......... 602/5, 20–21, 602/60–64, 12, 26; 606/201–204
See application file for complete search history.

(56) References Cited

U.S. PATENT DOCUMENTS

| 5,606,745 | A | | 3/1997 | Gray |
| 5,662,595 | A | | 9/1997 | Chesher et al. |
| 5,836,902 | A | * | 11/1998 | Gray .................... 602/5 |
| 5,934,599 | A | | 8/1999 | Hammerslag |
| 6,202,953 | B1 | | 3/2001 | Hammerslag |
| 6,289,558 | B1 | | 9/2001 | Hammerslag |
| 2002/0095750 | A1 | | 7/2002 | Hammerslag |
| 2003/0204938 | A1 | | 11/2003 | Hammerslag |
| 2006/0156517 | A1 | | 7/2006 | Hammerslag et al. |

OTHER PUBLICATIONS

Information Disclosure Statement (IDS) Letter Regarding Common Patent Application(s), submitted by Applicant on Apr. 6, 2009.

* cited by examiner

*Primary Examiner* — Kim M Lewis
(74) *Attorney, Agent, or Firm* — Tillman Wright, PLLC; Chad D. Tillman; Jeremy C. Doerre

(57) ABSTRACT

A method of making a wrist support includes molding a first section such that it is configured to receive a forearm, molding a second section such that it is configured to receive a hand, and molding a bridging section that is integrally formed with the first section and extends between and connects together the first section and the second section. The bridging section is generally flexible and recoverable and permits flexing of the second section relative to the first section in a radial-ulnar plane when a forearm is received by the first section of the wrist support and a hand is received by the second section of the wrist support, the bridging section biasing the first section and the second section toward a particular disposition relative to each other.

19 Claims, 8 Drawing Sheets

METHOD OF MAKING WRIST SUPPORT FOR JOINT POSITIONING

CROSS-REFERENCE TO RELATED APPLICATIONS

The present application is a continuation of, and claims the benefit of priority under 35 U.S.C. §120 to, U.S. patent application Ser. No. 11/187,589, pending, filed Jul. 22, 2005, which '589 application published as US 20060015980 and which '589 application is a continuation-in-part patent application of U.S. design patent application Ser. No. 29/209,985, filed Jul. 22, 2004, now U.S. Design Pat. No. 520,141, and which '589 application is a nonprovisional patent application of, and claims the benefit of priority under 35 U.S.C §119(e) to, U.S. provisional patent application Ser. No. 60/590,941, expired, filed Jul. 22, 2004. Each of these patent applications, patent, and patent application publication is incorporated herein by reference.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

Many wrist supports for disposition on an arm proximal or about a wrist are available. There are supports for preventing wrist flexion or for maintaining a particular disposition of a hand relative to a forearm. Typical such supports, having hard-shell or rigid beam components, are not conveniently adjusted with regard to the disposition of the hand relative to the forearm. There are supports for use in supporting active wrist flexion. These supports generally include complex hinging contraptions having rigid members and highly localized hinging axes about which a wrist may be forced to conform if flexing is to be achieved. Accordingly, a demand exists for one or more wrist supports that improve upon the braces currently available.

SUMMARY OF THE INVENTION

A first aspect of the invention generally relates to a joint support and, more particularly, to a wrist support having a first section for receiving a forearm, a second section for receiving a hand, and a bridging section extending between and connecting together the first section and second section. The bridging section is integrally formed in a molding step with at least a portion the first section or a portion of the second section. The bridging section spans the wrist and permits the second section to flex in a radial-ulnar plane relative to the first section. Optionally, the bridging section includes an intermediate portion having a height that is greater than its width. Also optionally, the wrist support includes one or more straps for securing the support in its disposition proximal a wrist.

In this first aspect, the wrist support may also include a tensioning line that extends along the bridging section. Tension in the tensioning line governs the disposition of the second section relative to the first section. A rotary device may be included for effecting adjustments in the tension of the tensioning line, thereby effecting adjustments to the wrist support.

These and other aspects and features of the present invention will be disclosed in connection with detailed descriptions of embodiments in accordance with the present invention set forth below.

BRIEF DESCRIPTION OF THE DRAWINGS

One or more embodiments of the present invention will be described in detail with reference to the accompanying drawings, which are briefly described below, wherein the same elements are referred to with the same reference numerals, and wherein various elements are not necessarily shown in conformance to any particular absolute or relative scale.

DETAILED DESCRIPTION

Figure 1:
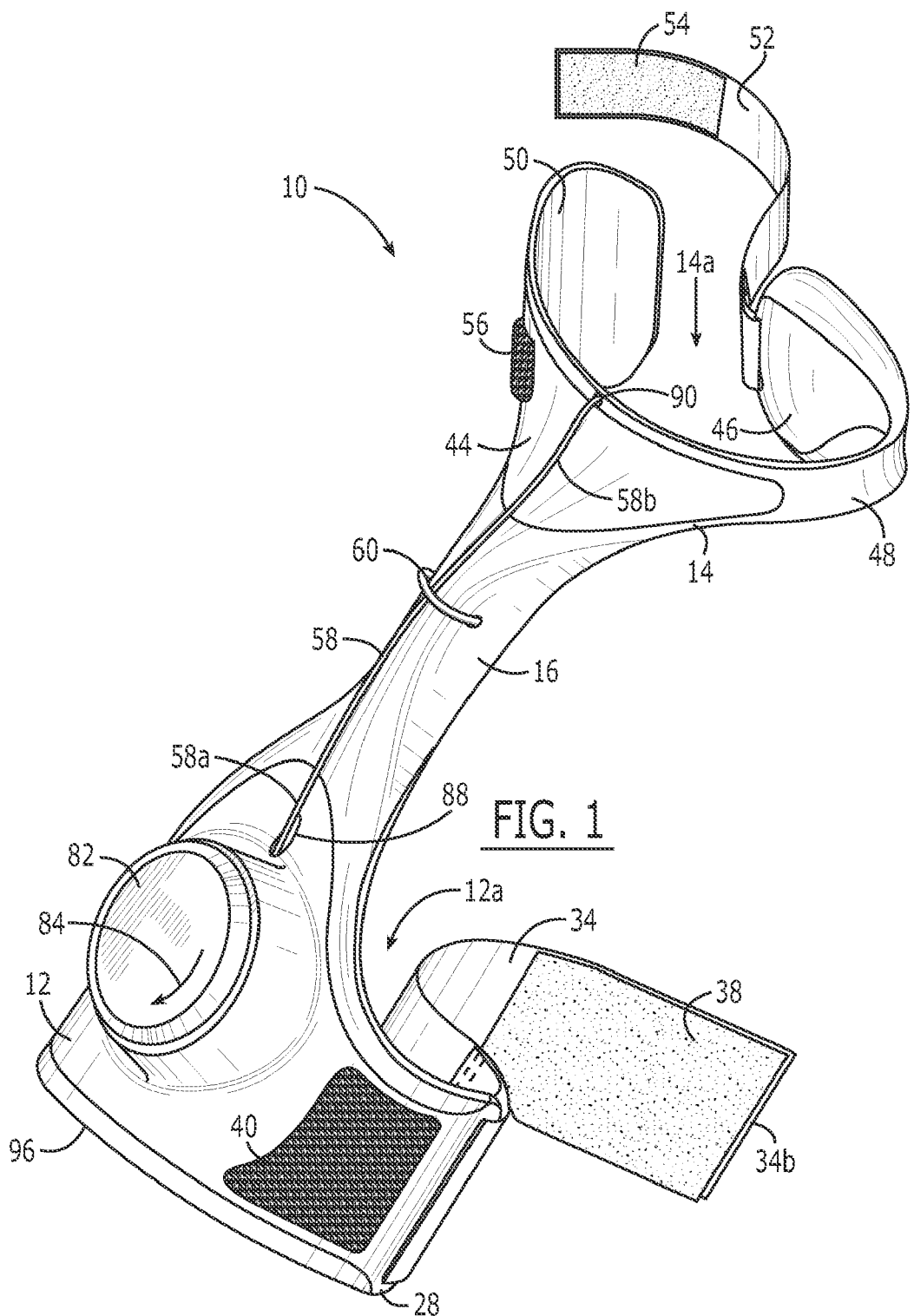
FIG. 1 is a perspective view of a first embodiment of the invention.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Additionally, several terms such as "dorsal," "volar," "radial," and "ulnar" are used herein with reference to features of the human hand. Indeed, descriptions herein of one or more illustrated embodiments of the invention sometimes are made with such terms that may imply that the embodiment is disposed on a forearm and hand. Use of such terms of reference is made herein in order to facilitate an understanding of the invention, and the forearm and the hand are not considered in such embodiments to be actual elements of the invention.

For the purpose of interpreting these terms of reference, consider a forearm and open hand resting palm-side down upon a planar desktop, with the forearm and palm generally contacting the desktop, and with the fingers and thumb generally straight and resting their lengths on the desktop. The volar sides of the forearm, wrist, hand, and fingers are generally disposed toward and contact the desktop. Thus, the fingerprints generally are found on the volar sides of fingertips. The dorsal sides of the forearm, wrist, hand, and fingers generally face in opposite direction to the volar sides of the forearm, wrist, hand, and fingers. These dorsal sides thus would be generally oriented away from the desktop. For example, fingernails generally grow from the dorsal sides of the fingers. The side of the hand from which the thumb depends defines the radial sides of the forearm, wrist, and hand. In contrast, the side of the hand opposing the radial side defines the ulnar sides of the forearm, wrist, and hand. For example, the fourth finger from the thumb of the hand, generally the smallest finger often called the "pinkie" finger, depends from the ulnar side of the hand. In view of these clarifications, these terms of reference are unambiguous and are well-defined with regard to essentially any hand or wrist, including both the left hand and right hand.

Regarding the views of the figures, dorsal views herein refer to views directed toward dorsal sides. For example, a dorsal view of a hand shows the dorsal side of the hand, which side is sometimes called the back of the hand. Similarly, a radial view of a hand would include a showing of the thumb, a volar view of a hand would include a showing of the palm, and an ulnar view of a hand would include a showing of the fourth finger from the thumb.

Regarding planes and axes, volar-dorsal planes are generally perpendicular to radial-ulnar planes, and the forearm generally defines a longitudinal axis. Consider again the forearm and hand resting palm-side down on a planar desktop, particularly when the hand and forearm are comfortably aligned and the fingers are extended straight and held tightly together. In this disposition of the forearm and hand, the plane of the desktop defines a radial-ulnar plane; a longitudinal axis is defined along the length of the forearm; and the four fingers of the hand extend generally parallel to the longitudinal axis. Furthermore, rotation of a radial-ulnar plane by ninety degrees about the longitudinal axis produces a volar-dorsal plane. For example, when a postcard is slipped between adjacent fingers such that an edge of the postcard abuts the desktop and is held parallel to the longitudinal axis, and such that the postcard stands vertically and ninety degrees from the plane of the desktop, the postcard defines a volar-dorsal plane.

It should be furthermore understood that the views of supports found in the accompanying drawings relate to a left forearm, wrist, and hand. For example, an image of a left hand appears in the environmental view of FIG. 6. Nevertheless, the accompanying drawings, and the descriptions herein, by the use of well-defined unambiguous terms, relate as well to braces adapted for a right forearm, wrist, and hand.

Turning now the figures, a first embodiment of the invention is shown in FIGS. 1-4, wherein a wrist support 10 comprises a first section 12 for receiving a forearm, a second section 14 for receiving a hand, and a bridging section 16 extending between and connecting together the first section 12 and the second section 14. The bridging section 16 permits flexing of the second section 14 relative to the first section 12, particularly in a radial-ulnar plane. That is, the bridging section 16 permits flexing of the second section 14 in a radial direction 18 (FIG. 2) and in an ulnar direction 20 relative to the first section 12.

The bridging section 16 preferably comprises an elastomeric material that is generally flexible and recoverable. The bridging section 16 generally maintains or biases the second section 14 to obtain a particular disposition, for example that of FIGS. 2-3, relative to the first section 12. However, when forces in radial and ulnar directions 18,20 are present, such as when the wrist support 10 is donned and a hand is flexed in radial and ulnar directions, the bridging section 16 particularly accommodates such flexing.

Figure 2:
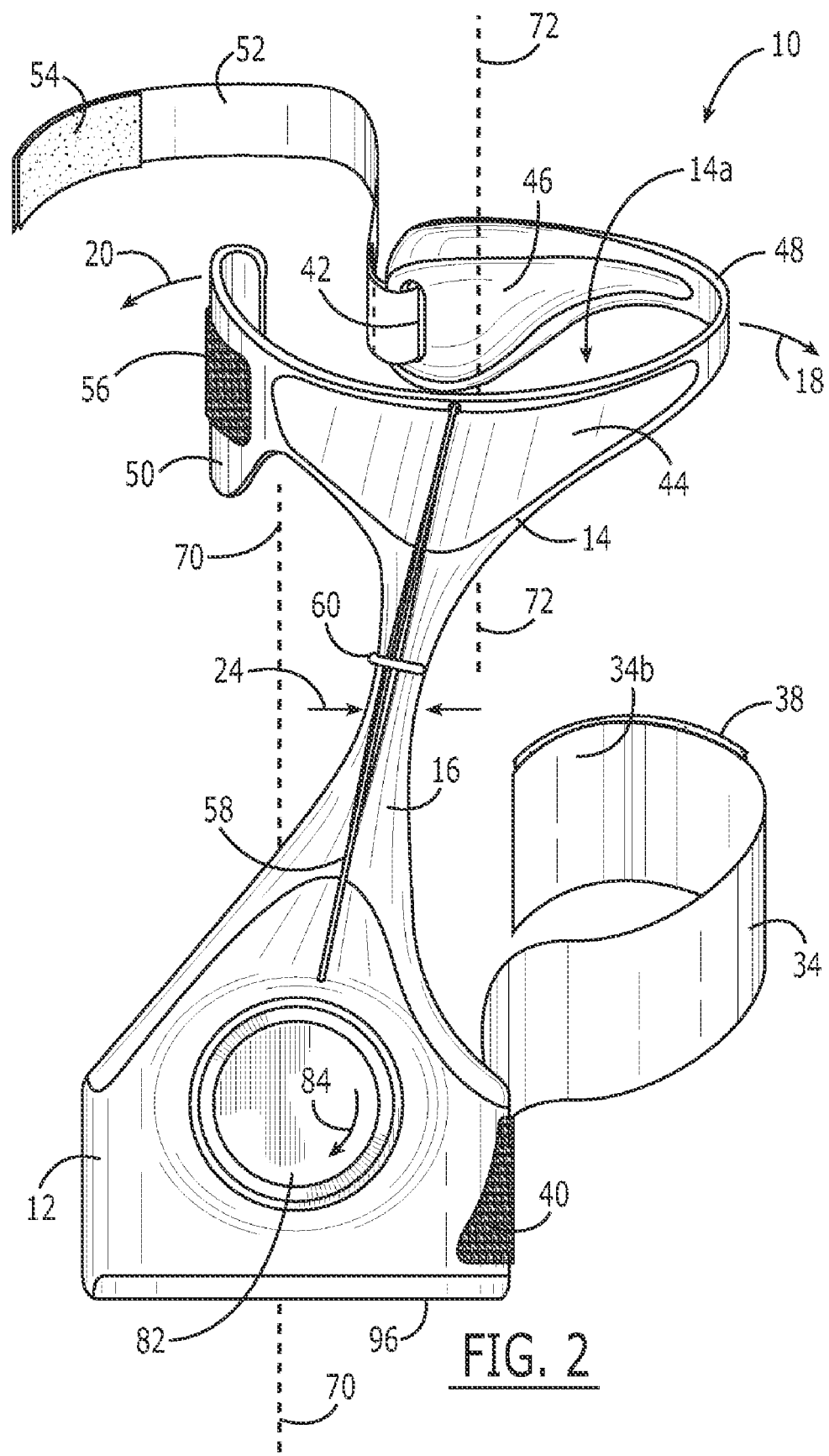
FIG. 2 is a dorsal plan view of the embodiment of FIG. 1.
Figure 3:
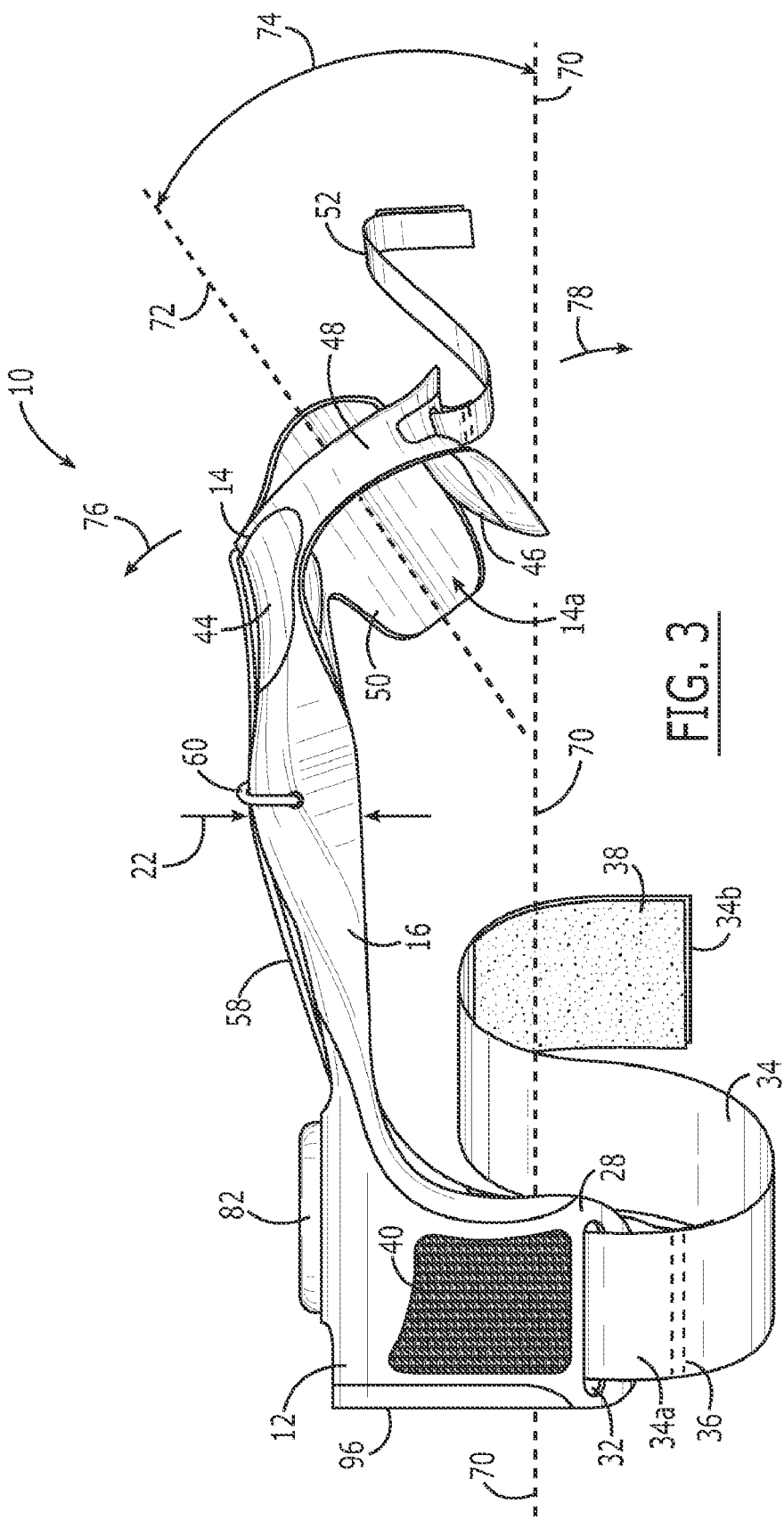
FIG. 3 is a radial side view of the embodiment of FIG. 1.

As shown in FIGS. 2-3, the bridging section includes an intermediate portion preferably having a height 22 (FIG. 3) in a volar-dorsal plane that is greater its width 24 (FIG. 2) in a radial-ulnar plane. The bridging section, at least in the intermediate portion thereof where the height 22 and width 24 are defined, thereby is particularly more flexible with regard to flexions in the radial direction 18 and the ulnar direction 20 than in the volar direction and the dorsal direction.

The first section 12 of the wrist support 10 is adapted to receive a forearm and releasably retain the forearm. An arcuate forearm pad 96 (FIGS. 1-4) is attached to a margin of the first section 12 of the wrist support 10 and, optionally, is formed of the same material as the bridging section 16 described in detail below.

Figure 4:
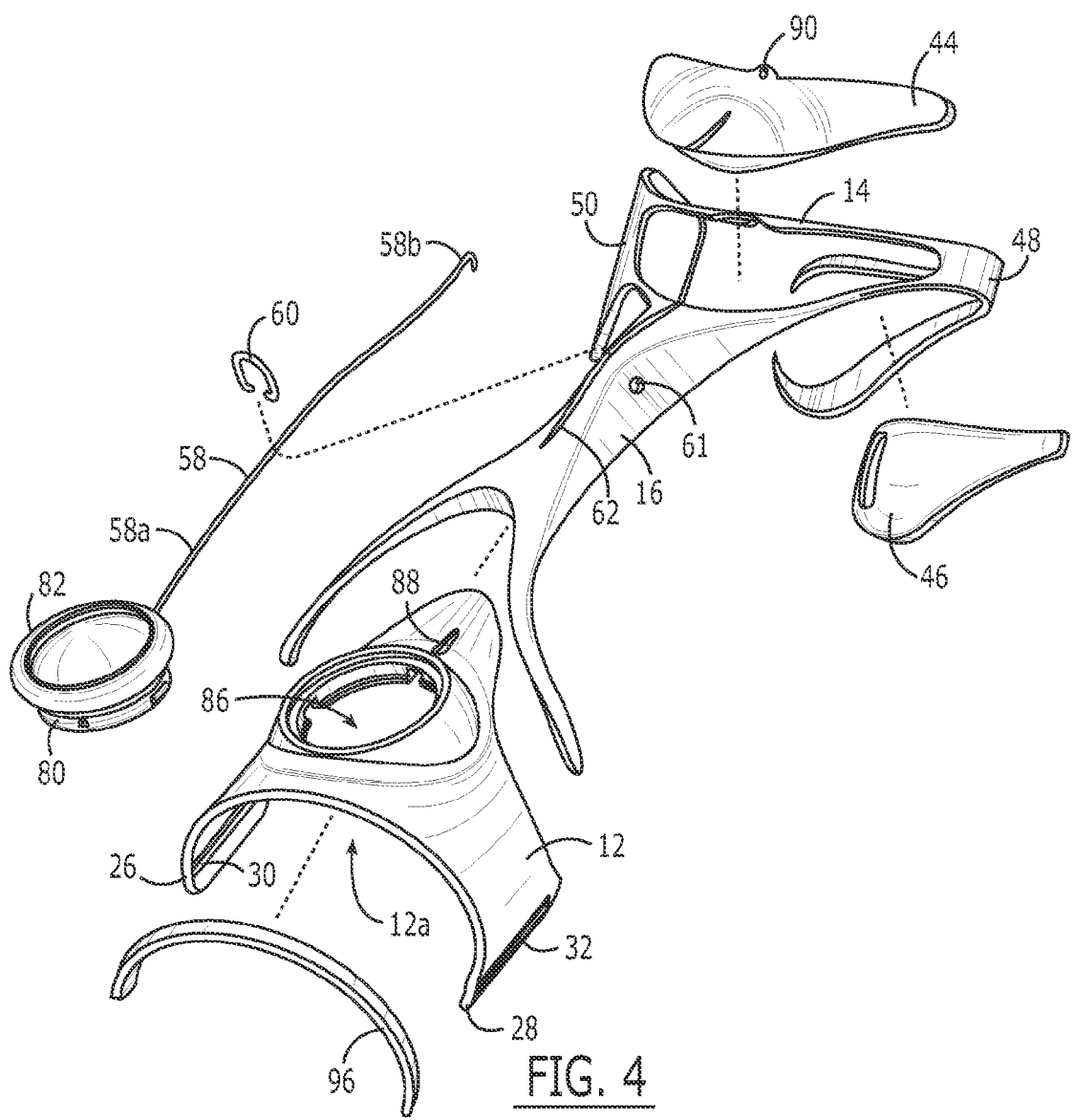
FIG. 4 is an exploded perspective view of the embodiment of FIG. 1.

The first section 12 optionally retains the forearm by way of a strap. For example, as shown in FIG. 4, the first section 12 comprises a forearm-receiving area 12a defined between opposing end portions 26,28 that further define respective strap attachment openings 30,32 for receipt there through of a first strap 34 (FIGS. 1-3). The first strap is shown as affixed at one end 34a (FIG. 3) thereof to the end portion 28 of the first section 12, for example by stitching 36.

When the wrist support 10 is donned (not shown) such that the dorsal side of a forearm is received by the receiving area 12a (FIGS. 1,4), which receiving-area 12a is contoured to fit the dorsal side of the forearm. The second end 34b of the first strap 34 also is generally passed through the strap attachment opening 30 defined in the end portion 26 (FIG. 4) such that the forearm is completely encircled by the first section 12 and the first strap 34. The second end 34b of the first strap is releasably fastened to securely maintain the encirclement such that the forearm is releasably retained in the forearm-receiving area 12a.

For example, the first strap 34 optionally has a fastener 38 for fastening the second end thereof to a fastener 40 of the first section 12. In the illustrated example, the fastener 38 of the first strap comprises loops whereas the fastener 40 of the first section 12 comprises hooks that releasably engage loops in hook-and-loop engagement. Such hook-and-loop fasteners are commonly sold and known by the trademark VELCRO. In other examples, fasteners include buttons, snaps, hooks and eyelets, clasps, zippers, and adhesives such as that of replaceable fabric sports tape.

The second section 14 of the wrist support 10 is configured to receive and releasably retain a hand. In particular, the second section 14 comprises a dorsal portion 44 (FIG. 2), a volar portion 46 attached to the dorsal portion 44 by way of a radial portion 48, and an ulnar portion 50 attached to the dorsal portion 44. A hand-receiving area 14a (FIGS. 1-3) is defined between the dorsal portion 44 and volar portion 46, and between the radial portion 48 and the ulnar portion 50. A strap is optionally adapted for releasably retaining a hand (not shown) in the receiving area 14a.

In the illustrated example, a strap attachment opening 42 (FIG. 2) is defined by the volar portion 46. A second strap 52 is shown as affixed to the volar portion 46, for example by way of stitches. The second strap 52 comprises a fastener 54 for releasably fastening the strap 52 to a fastener 56 of the ulnar portion 50. In the illustrated example, the fastener 54 of the second strap comprises loops whereas the fastener 56 of the ulnar portion 50 comprises hooks that releasably engage loops in hook-and-loop engagement. In other examples, fasteners include buttons, snaps, hooks and eyelets, clasps, zippers, and adhesives such as that of replaceable fabric sports tape.

When the wrist support is donned (not shown) such that a hand is received by the receiving area 14a and the second strap 52 is fastened to the ulnar portion 50, the hand is completely encircled by the second section 14 and the second strap 52, the second section comprising the dorsal portion 44, the radial portion 48, the volar portion 46, and the ulnar portion 50.

Whereas various materials and methods of forming of wrist supports and portions thereof are within the scope of the descriptions herein, in the first embodiment of FIGS. 1-4, the bridging section 16 preferably is integrally formed in a molding step with at least a portion of one of the first section 12 and the second section 14. That is, the bridging section 16 is integrally formed in a molding step with at least a portion of the first section 12, or, the bridging section is integrally formed in a molding step with at least a portion of the second section 14, or, the bridging section is integrally formed in a molding step with respective portions of both of the first section and the second section.

In a particular example, the bridging section 16 and portions of the second section 14 are formed in an injection molding step from a first elastomeric material, and the first section is formed in a different molding step from a different material. In this example, the bridging section 16 (FIG. 1) and both the radial portion 48 and the ulnar portion 50 of the second section 14 all are integrally formed in a single molding step from a first elastomeric material. Further in this example, the first section 12 is formed in another injection molding step from a rigid or semi-rigid material, and both the dorsal portion 44 and the volar portion 46 of the second section 14 are formed from a rigid or semi-rigid material.

Exemplary elastomeric materials include, but are not limited to: thermoplastic elastomers; silicone; high temperature silicone; elastomeric plastics, particularly moldable and injection-moldable plastics; and rubber.

Exemplary rigid or semi-rigid materials include, but are not limited to: plastics, particularly moldable and injection-moldable plastics; Nylon 66; fiberglass; carbon and carbon composites; polycarbonate; polyoxymethylene; polymethyl-methacrylate (PMMA); polyacetal; urea-formaldehyde; polystyrene; and vinyl polymers.

As shown in FIGS. 1-4, the wrist support 10 further comprises a tensioning line 58 that extends along the bridging section 16 between the first section 12 and the second section 14. The tensioning line is utilized to apply tension between the first section and second section. Optionally, a tension line guide 60 is disposed on the bridging section 16 for guidance of the tensioning line 58.

In the first embodiment of the wrist support 10, the tension line guide 60 comprises an arcuate wire bail having ends disposed in detents 61 or holes (FIG. 4) of the bridging section 16. The tensioning line 58 passes through the tension line guide for maintenance of the tensioning line in its intended disposition along the extent of the bridging section 16. For further guiding of the tensioning line 58, a channel 62 (FIG. 4) optionally is formed in the bridging section 16.

The bridging section 16 generally biases the second section 14 to obtain a particular disposition, for example that of FIGS. 2-3, relative to the first section 12, wherein the particular disposition is variable according to the effective length of the tensioning line 58. The first section 12 defines a first axis 70 along which the first section is adapted to receive a forearm (not shown), such that the first axis 70 is parallel and optionally coincident with the longitudinal axis of the forearm. The second section 14 defines a second axis 72 along which the second section 14 is adapted to receive a hand (not shown). As shown in FIG. 3, an angle 74 is defined between the first axis 70 and the second axis 72. The disposition of the second section 14 relative to the first section 12 is defined by, among other things, the angle 74.

As the bridging section 16 preferably comprises a elastomeric material that is flexible and recoverable, and as tension in the tensioning line 58 generally applies torque about the bridging section, shortening the tensioning line, which is attached at respective ends thereof to the first and second sections 12,14, generally increases the tension of the line and thereby causes flexing of the bridging section 16, particularly in the dorsal direction 76 (FIG. 3). Subsequently re-lengthening the tensioning line generally decreases the tension of the line thereby allowing the flexed bridging section to return toward the volar direction 78. Thus, in a sense, the bridging section 16 comprises a continuous hinge extending between the first section 12 and the second section 14, in that a single hinging axis passing through the bridging section 16 is not necessarily uniquely defined by flexions of the bridging section. The bridging section 16 preferably is capable of stretching and recovering so that it conforms to the exterior of the wrist allowing a hand to flex relative to a forearm about axes within the wrist.

Flexing of the bridging section 16 in the dorsal direction causes the second section 14 to travel in the dorsal direction relative to the first section 12 and causes the second axis 72 to rotate away from the first axis 70 thereby increasing the angle 74. A return of the flexed bridging section 16 toward the volar direction allows the second section 14 to return toward the volar direction relative to the first section 12 and allows the second axis 72 to return toward the first axis 70 thereby decreasing the angle 74.

The volar-dorsal flexions of the bridging section 16 and the relative disposition of the second section 14 to the first section 12 are thereby related to the tension and length of the tensioning line 58. In particular, insofar as the tensioning line is taut, tension in the tensioning line 58 generally precludes the angle 74 from decreasing by restraining movement of the second section 14 in the volar direction 78 relative to the first section 12. Adjustments in the length of the tensioning line 58 generally thereby effect adjustments in the angle 74.

For convenient adjustments of the length of the tensioning line 58, the wrist support 10 further comprises an adjustment mechanism such as a rotary device 80 (FIG. 4). The rotary device is operable to adjust the effective length of the tensioning line 58 which extends from the device as shown in FIG. 4. The rotary device includes a rotatable control knob 82 (FIGS. 1-4) for grasping by a user in controlling the device and in adjusting the wrist support. Upon rotation of the rotatable control knob 82 in a first rotational direction 84, a portion of the tensioning line 58 is drawn into the rotary device 80, thereby effectively shortening the line for adjusting the angle 74, specifically increasing the angle 74 (FIG. 3). Furthermore, by pressing of the rotatable control knob 82, a portion of the tensioning line 58 preferably is released from the device, thereby effectively lengthening the line for adjusting the angle 74, specifically decreasing the angle 74.

It should be understood that, while the first rotational direction 84 is illustrated as being clockwise in FIGS. 1-2, the descriptions herein relate to counterclockwise rotations as well. Thus, the wrist support of the first embodiment is variably adjusted, with regard to the disposition of the second section relative to the first section, by rotating and pressing the control knob 82.

An exemplary rotary device is described in U.S. Pat. No. 5,042,177 titled "Rotary Closure for a Sports Shoe, Especially a Ski Shoe," which patent is hereby incorporated herein by reference.

In another embodiment of the invention, not illustrated, components of a wrist support are adjusted from a first relative disposition to a second relative disposition upon rotation of a control knob in one rotational direction, and are subsequently returned to the first relative disposition upon rotation of the control knob in an opposite rotational direction. That is, in this other embodiment, the wrist support is variably adjusted by rotations of a control knob in opposite rotational directions.

In yet another embodiment of the invention, not illustrated, a wrist support is adjusted with regard to the relative dispositions of the sections 12,14 thereof by rotation of a control knob and by pulling of the knob outwardly from the support to release the tensioning line wound therein.

It should be apparent that the present invention has many embodiments and the descriptions herein of particular rotary devices are provide as examples and are not to be construed as limitations of the invention.

The rotary device 80 (FIG. 4) of the wrist support 10 is received by a receiving area 86 defined by the first section 12. The rotary device 80 snaps securely into and is retained within the receiving area 86. A first end 58a of the tensioning line 58 is passed through a grommet 88 formed in the first section 12 and extends there from along the bridging section 16 as shown in FIG. 1. An opposing end 58b of the tensioning line distal the rotary device 80 is attached, as shown in FIG. 1, to the dorsal portion 44 of the second section 14 at a grommet 90 (FIG. 4).

In FIG. 3, the wrist support 10 is shown as having obtained a disposition of the second section 14 relative to the first section 12, wherein the disposition is defined by, among other things, the angle 74 between the first axis 70 and the second axis 72. It should be understood that the wrist support 10 is dynamic and is variably adjustable according to rotations of the control knob 82. Thus, FIG. 3 relates to a snapshot view of a dynamic wrist support, wherein, in this snapshot, the tensioning line 58 is taut, but does not appreciably flex the bridging section 16. That is, the wrist support 10 is shown in FIGS. 1-3 as having obtained a disposition preferred by the formation of the bridging section 16, though the wrist support 10 can nonetheless obtain other dispositions by forcible flexing of the bridging section 16.

It furthermore should be understood that no numeric value is given herein with reference to the angle 74, and it should be understood that the angle according to the preferred disposition is predetermined according to considerations that can include, but are not limited to: the comfort of the wearer of the wrist support; the activities for which the wrist support is adapted; and, the prescription of a health care provider.

In the first embodiment of the invention, the tensioning line 58 comprises a flexible and inextensible line. The tensioning line is illustrated in FIGS. 1-4 as a monofilament line though these descriptions relate as well to multifilament lines and many types of elongate flexible lines having various constructions and formed of various materials having respective tensile and flexible properties.

Exemplary constructions include, but are not limited to: monofilament lines, multifilament lines, wound lines, woven lines, braided lines, layered lines, strings, ropes, cords, threads, twines, intertwined strands, chains, tethers, belts, bands, straps, and combinations thereof.

Exemplary materials include, but are not limited to: natural fibers including hemp, cotton, linen, hide, gut, and sinew; synthetic and plastic fibers such as nylon, polyethylene, and fluorocarbon; lines formed of metals such as wires and cables, in particular wound steel cables; and, combinations thereof.

The first and second sections 12,14 are each optionally padded for comfort of the wearer of the wrist support 10. Padding, when present, preferably comprises soft materials, which optionally may be detachable for washing. Exemplary materials include, but are not limited to, natural and synthetic fabrics, pliable foams, elastic fabrics, neoprene, spandex, felt, natural and synthetic chamois, and various elastomeric materials.

Turning now to a second embodiment shown in various views in FIGS. 5-8, a wrist support 110 comprises a first section 112 for receiving a forearm, a second section 114 for receiving a hand, and a bridging section 116 extending between and connecting together the first section and second section. The bridging section 116 permits flexing of the second section 114 relative to the first section 112, particularly in a radial-ulnar plane. That is, the bridging section 116 permits flexing of the second section 114 in a radial direction 118 (FIG. 6) and in an ulnar direction 120 relative to the first section 112.

The bridging section 116 preferably comprises an elastomeric material that is generally flexible and recoverable. The bridging section 116 generally maintains or biases the second section 114 to obtain a particular disposition, for example that of FIGS. 6-7, relative to the first section 112. However, when forces in radial and ulnar directions 118,120 are present, such as when the wrist support 110 is donned and a hand is flexed in radial and ulnar directions, the bridging section 116 particularly permits such flexing.

The wrist support 110 of FIGS. 5-8 bears many similarities to the wrist support 10 of FIGS. 1-4. Therefore, many of the descriptions herein relate to both apparatus 10 and apparatus 110. However, in the interest of providing descriptions of the present invention that has many embodiments, and in the interest of minimizing duplicative descriptions, the descriptions below relate particularly to features and benefits of the wrist support 110 that are generally not merely duplicative to those of the wrist support 10.

Figure 6:
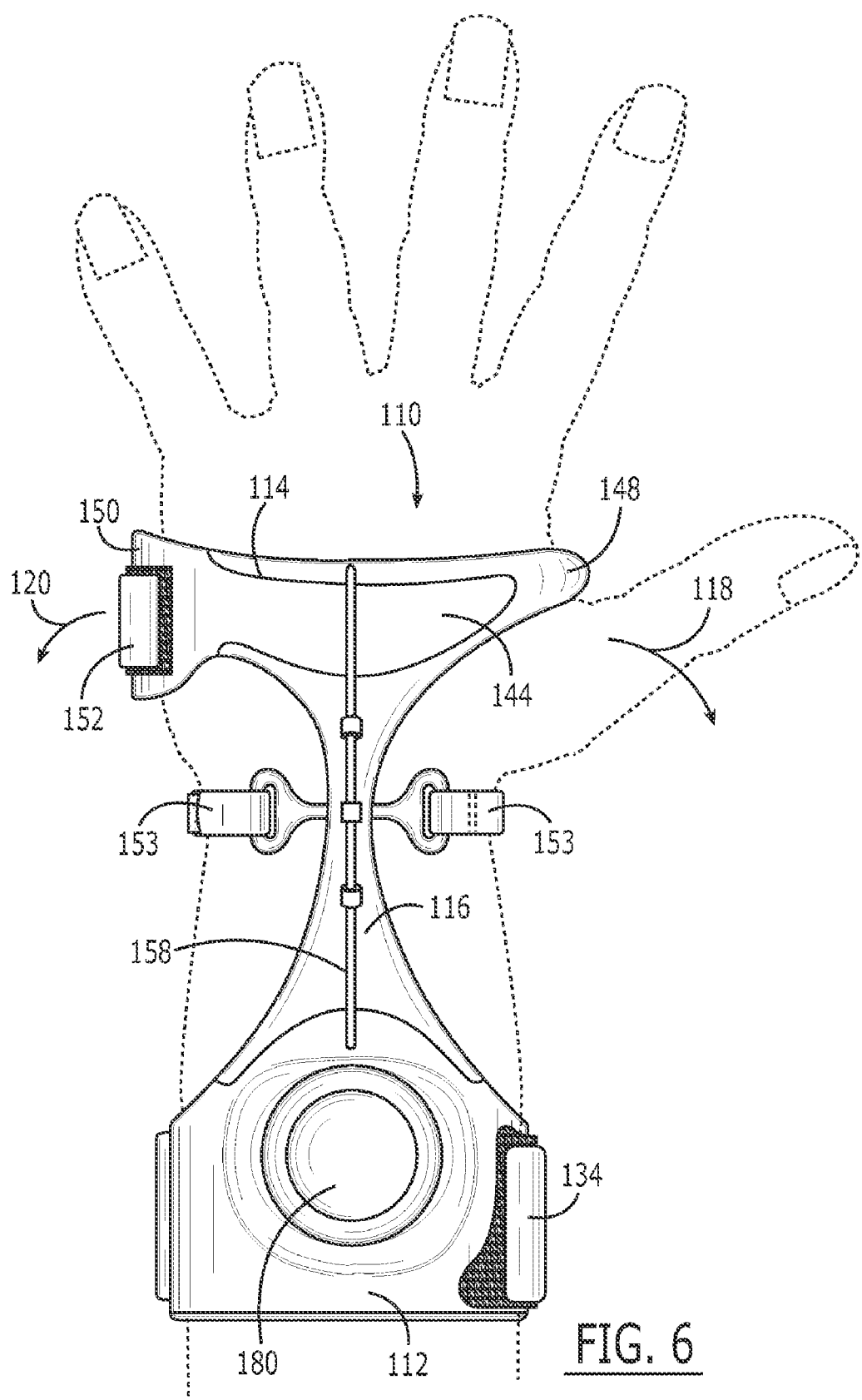
FIG. 6 is an environmental dorsal plan view of the embodiment of FIG. 5.
Figure 7:
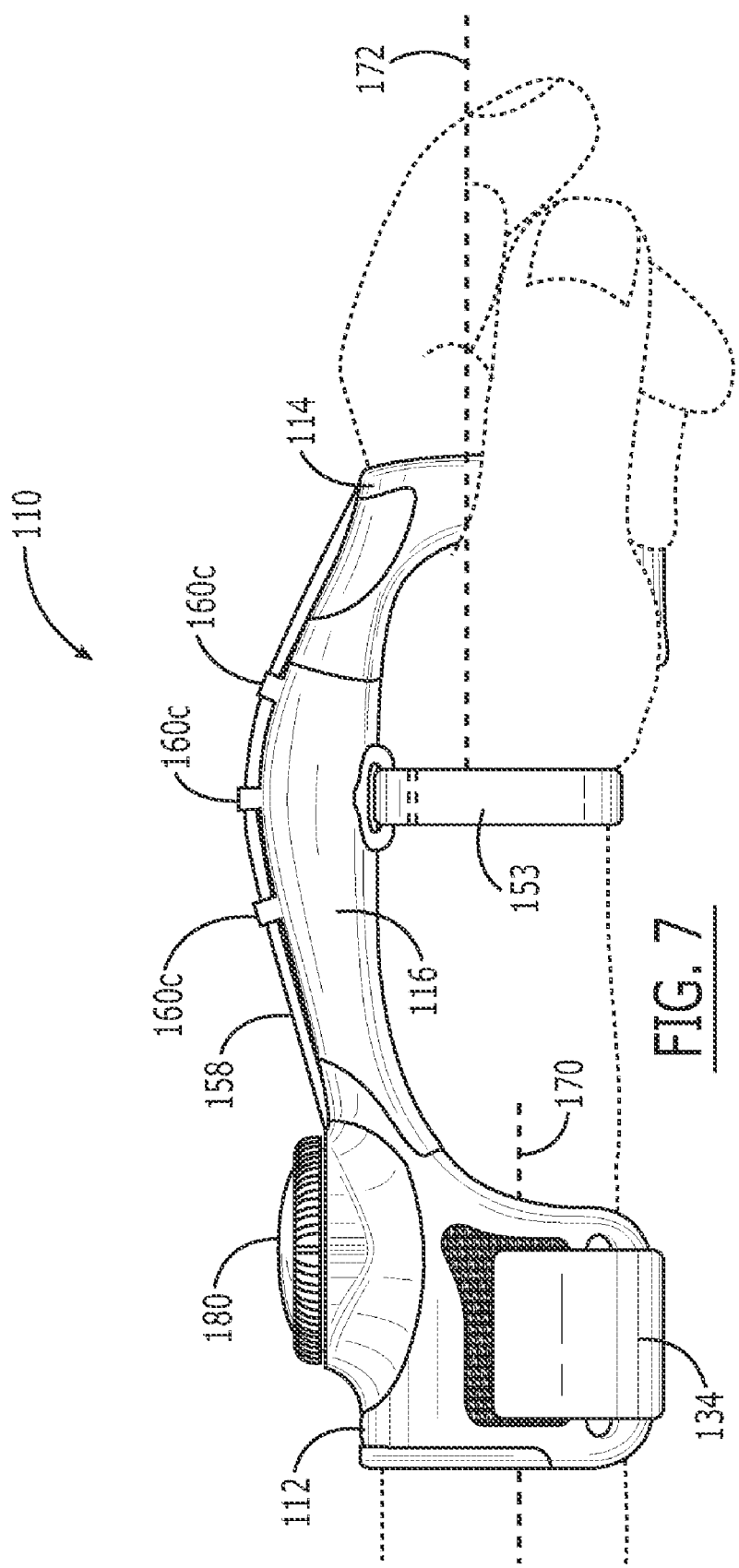
FIG. 7 is an environmental radial side view of the embodiment of FIG. 5.
Figure 8:
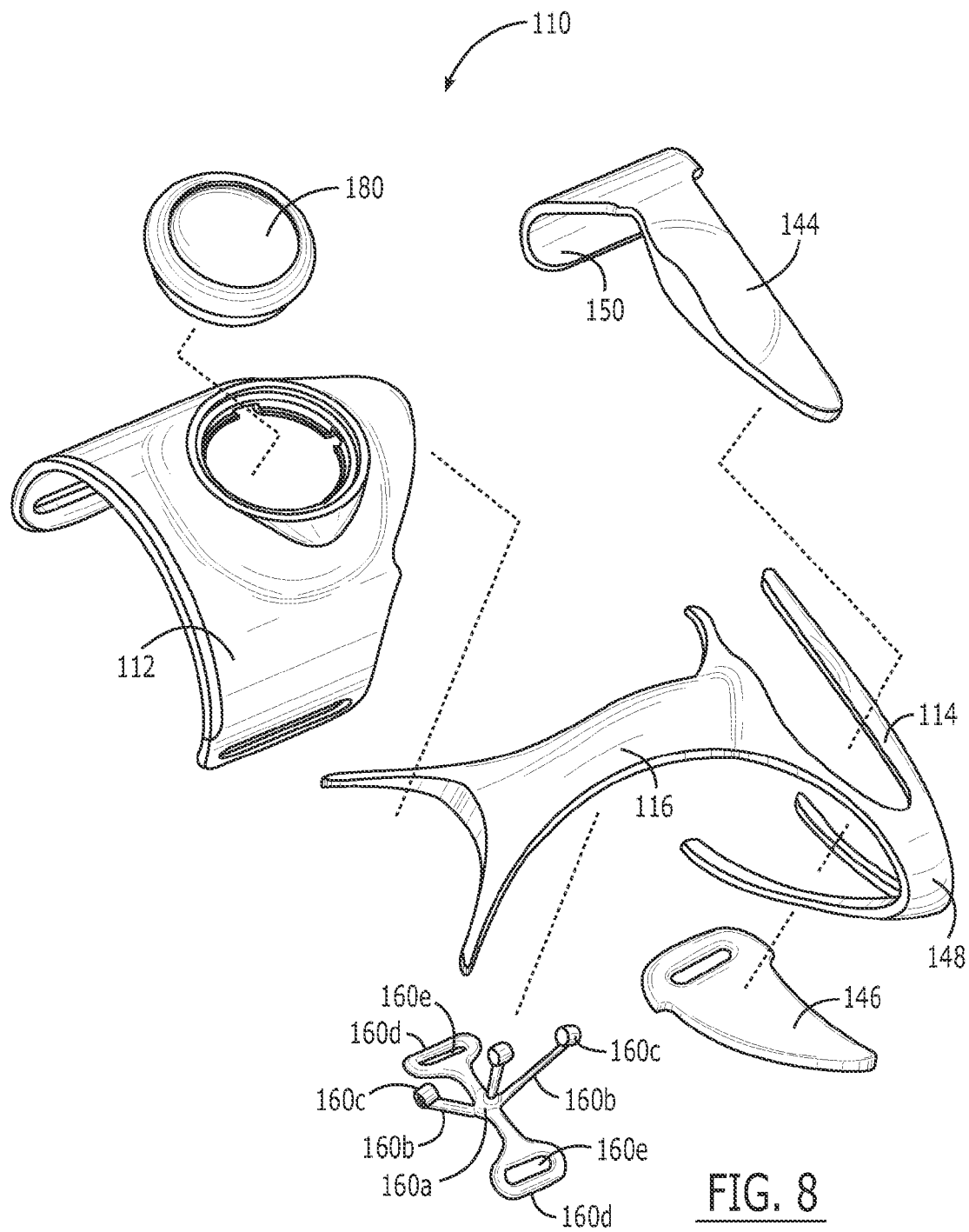
FIG. 8 is an exploded perspective view of the embodiment of FIG. 5.

For example, whereas the wrist support 10 (FIG. 3) is shown as having obtained a disposition preferred by the bridging section 16 such that the second axis 72 and the first axis 70 are disposed at an appreciable distance in the radial-ulnar plane (FIG. 2) and at an angle 74 to one another (FIG. 3), the wrist support 110 is shown in FIG. 7 as having obtained a disposition preferred by the bridging section 116 wherein the second axis 172 defined by the second section 114 essentially extends in a parallel plane with the first axis 170 defined by the first section 112. Furthermore, the first axis 170 and second axis 172 may extend parallel to one another when the axes 170,172 additionally are aligned as shown in FIG. 6. That is, while the wrist support 10 (FIG. 3) is constructed to prefer a dorsal flexion of the hand relative to the forearm (a dorsiflexed wrist), the wrist support 110 (FIG. 7) is constructed to prefer alignment of the hand with the forearm (an unflexed or neutral wrist).

In another embodiment (not shown), a wrist support is constructed to prefer a volar flexion of the hand relative to the forearm (a volar-flexed wrist).

Therefore in view of the wrist support 10 (FIG. 3) of the first embodiment, and in view of the wrist support 110 (FIG. 7) of the second embodiment, it should be understood that preferred dispositions of various other embodiments relate to wrist flexions in dorsal, volar, radial, and ulnar directions, and combinations thereof, according to considerations that can include, but are not limited to: the comfort of the wearer of the wrist support; the activities for which the wrist support is adapted; and, the prescription of a health care provider.

Figure 5:
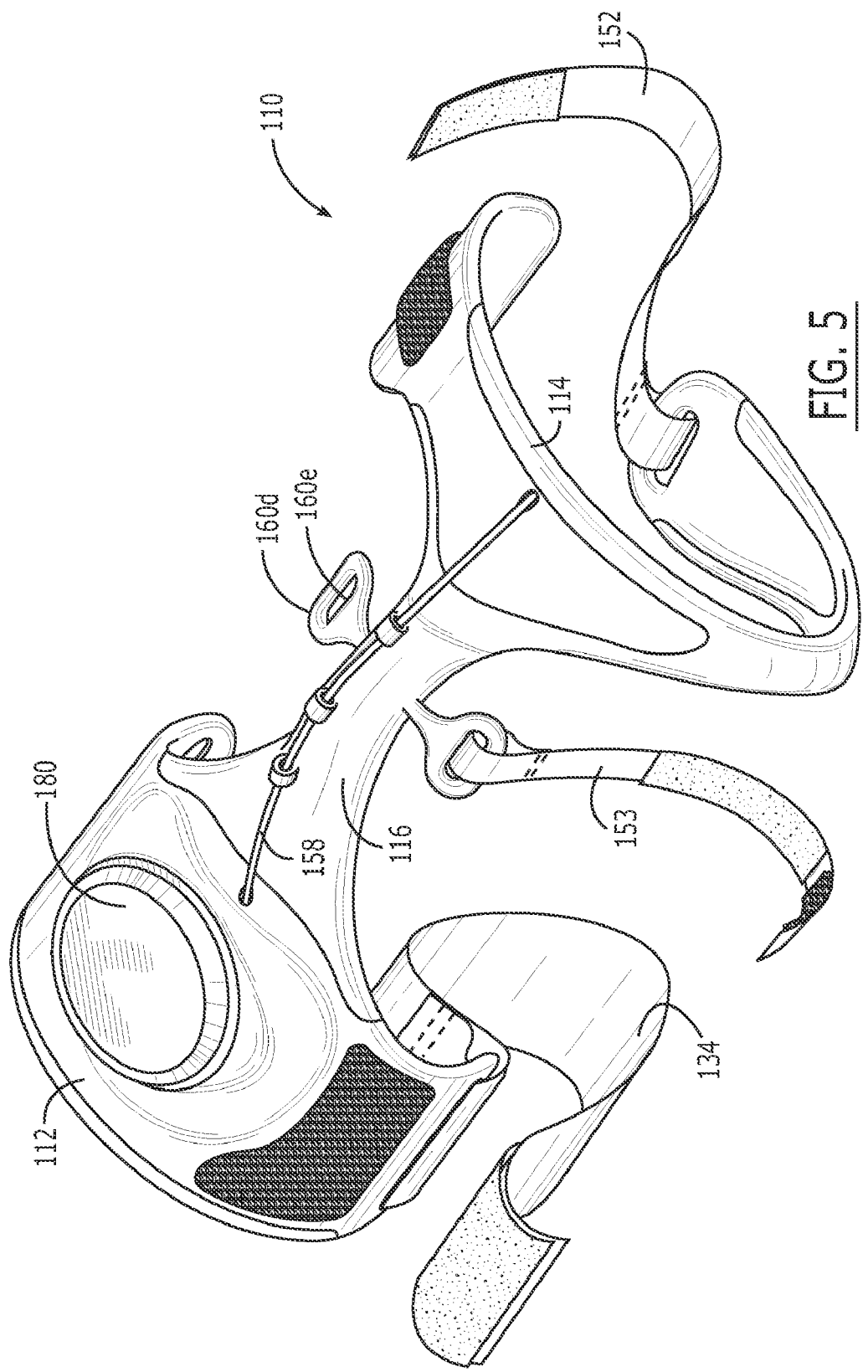
FIG. 5 is a perspective view of a second embodiment of the invention.

The second embodiment 110 further illustrates another feature of the present invention, wherein the tension line guide 160 (FIG. 8) comprises a hub 160a, multiple arms 160b depending from the hub 160a, and multiple grommets 160c attached respectively to the multiple arms 160b. The tensioning line 158 passes through and is guided along the bridging section 116 by the grommets 160c as shown in FIGS. 5-7.

In this embodiment, the arms 160b and hub 160a are disposed within the bridging section 116. For example, such disposition can be effected by molding of the bridging section 116 about the tension line guide 160. The tension line guide 160 thereby defines a skeletal structure disposed and captured within the bridging section 116.

Optionally, the bridging section 116 is formed of an elastomeric material and the tension line guide 160 is formed of a rigid or semirigid material.

In a variation of this feature, the tension line guide 160 of the second embodiment (FIG. 8) further comprises opposing members 160d which define respective strap attachment openings 160e. In this embodiment, the wrist support comprises a first strap 134 (FIG. 5) for securing the first section 112 to a forearm as shown in FIGS. 6-7, a second strap 152 (FIG. 5) for securing the second section 114 to a hand as shown in FIG. 6, and a third strap 153 (FIG. 5) for securing the bridging section 116 to a wrist which the bridging section 116 spans, as shown in FIG. 6. In securing the bridging section 116 to the wrist, the third strap 153 is passed through the strap attachment openings 160e of the tension line guide 160.

The second embodiment 110 further illustrates another feature of the present invention, wherein the dorsal portion 144 (FIGS. 6,8) and the ulnar portion 150 are integrally formed together, optionally of a first material that is different from the material from which the radial portion 148 is formed. The volar portion 146 also is optionally formed of a material that is different from the material from which the radial portion 148 is formed. For example, the radial portion 148 and the bridging section 116 optionally are integrally formed in a molding step of an elastomeric material while the dorsal portion 144 and volar portion 146 are optionally formed of a rigid or semirigid material.

Despite other differences in the first and second embodiments, in similarity to the bridging section 16 of the first embodiment, the bridging portion 116 is formed of a flexible and recoverable material such that the disposition of the second section 114 relative to the first section 112 is variable according to, among other things, the length and tension of the tensioning line 158 (FIGS. 5-7) as governed, at least in part, by the rotary device 180.

What is claimed is:

1. A method of making a wrist support, comprising the steps of:
   (a) molding a first section such that the first section is configured to receive a forearm;
   (b) molding a second section such that the second section is configured to receive a hand; and
   (c) molding a bridging section;
   (d) wherein the bridging section is integrally formed with one of the first section and the second section, and extends between and connects together the first section and the second section;
   (e) wherein the bridging section is generally flexible and recoverable and permits flexing of the second section relative to the first section in a radial-ulnar plane when a forearm is received by the first section of the wrist support and a hand is received by the second section of the wrist support, the bridging section biasing the first section and the second section toward a particular disposition relative to each other; and
   (f) wherein the bridging section is molded such that an intermediate portion of the bridging section has a height in a volar-dorsal plane that is greater than its width in the radial-ulnar plane.

2. The method of claim 1, further comprising providing a tensioning line such that the tensioning line extends between the first section and the second section for applying tension between the first section and the second section.

3. The method of claim 2, further comprising providing a rotary device on the first section configured to shorten a portion of the tensioning line extending between the first section and the second section for increasing the tension therebetween.

4. The method of claim 2, wherein said step of molding the bridging section comprises forming a guide channel in a surface of the bridging section that receives and guides the tensioning line between the first section and the second section.

5. The method of claim 1, wherein the bridging section is integrally formed with both the first section and the second section.

6. The method of claim 1, wherein the bridging section is integrally formed with only one of the first section and the second section.

7. A method of making a wrist support, comprising the steps of:
(a) molding a first section such that the first section is configured to receive a forearm;
(b) molding a second section such that the second section is configured to receive a hand; and
(c) molding a bridging section;
(d) wherein the bridging section is integrally formed with the second section, and extends between and connects together the first section and the second section;
(e) wherein the bridging section is generally flexible and recoverable and permits flexing of the second section relative to the first section in a radial-ulnar plane when a forearm is received by the first section of the wrist support and a hand is received by the second section of the wrist support, the bridging section biasing the first section and the second section toward a particular disposition relative to each other; and
(f) wherein the second section and the bridging section are integrally formed in said steps (b) and (c) from a first elastomeric material such that the second section and bridging section are generally flexible and recoverable, and wherein the first section is formed in said step (a) from a different material such that the first section is rigid.

8. The method of claim 7, wherein the method further comprises providing a tensioning line such that the tensioning line extends between the first section and the second section for applying tension between the first section and the second section.

9. The method of claim 8, further comprising providing a rotary device on the first section configured to shorten a portion of the tensioning line extending between the first section and the second section for increasing the tension therebetween.

10. The method of claim 8, wherein said step of molding the bridging section comprises forming a guide channel in a surface of the bridging section that receives and guides the tensioning line between the first section and the second section.

11. A method of making a wrist support, comprising the steps of:
(a) molding a first section such that the first section is configured to receive a forearm;
(b) molding a second section such that the second section is configured to receive a hand; and
(c) molding a bridging section;
(d) wherein the bridging section is integrally formed with one of the first section and the second section, and extends between and connects together the first section and the second section;
(e) wherein the bridging section is generally flexible and recoverable and permits flexing of the second section relative to the first section in a radial-ulnar plane when a forearm is received by the first section of the wrist support and a hand is received by the second section of the wrist support, the bridging section biasing the first section and the second section toward a particular disposition relative to each other; and
wherein the method further comprises providing a tensioning line such that the tensioning line extends between the first section and the second section for applying tension between the first section and the second section.

12. The method of claim 11, further comprising providing a rotary device on the first section configured to shorten a portion of the tensioning line extending between the first section and the second section for increasing the tension therebetween.

13. The method of claim 11, wherein said step of molding the bridging section comprises forming a guide channel in a surface of the bridging section that receives and guides the tensioning line between the first section and the second section.

14. The method of claim 11, wherein the bridging section is integrally formed with both the first section and the second section.

15. The method of claim 11, wherein the bridging section is integrally formed with only one of the first section and the second section.

16. A method of making a wrist support, comprising the steps of:
(a) molding a first section such that the first section is configured to receive a forearm;
(b) molding a second section such that the second section is configured to receive a hand; and
(c) molding a bridging section;
(d) wherein the bridging section is integrally formed with the first section and the second section, and extends between and connects together the first section and the second section;
(e) wherein the bridging section is generally flexible and recoverable and permits flexing of the second section relative to the first section in a radial-ulnar plane when a forearm is received by the first section of the wrist support and a hand is received by the second section of the wrist support, the bridging section biasing the first section and the second section toward a particular disposition relative to each other; and
wherein said step of molding the bridging section comprises forming the bridging section such that the bridging section comprises a single elongate member; wherein the first section, the second section, and the bridging section form a single molded piece; and wherein, out of the single molded piece, only the single elongate member of the bridging section extends between and joins the first section and the second section.

17. The method of claim 16, wherein the method further comprises providing a tensioning line such that the tensioning line extends between the first section and the second section for applying tension between the first section and the second section.

18. The method of claim 17, further comprising providing a rotary device on the first section configured to shorten a portion of the tensioning line extending between the first section and the second section for increasing the tension therebetween.

19. The method of claim 17, wherein said step of molding the bridging section comprises forming a guide channel in a surface of the bridging section that receives and guides the tensioning line between the first section and the second section.

* * * * *